United States Patent [19]

Tapp et al.

[11] Patent Number: 5,241,851
[45] Date of Patent: Sep. 7, 1993

[54] METHOD OF PERFORMING AN INSTANTANEOUS MOISTURE CONCENTRATION MEASUREMENT AND FOR DETERMINING THE DRYDOWN CHARACTERISTICS OF AN ENVIRONMENT

[75] Inventors: Frederick Tapp, Hillsborough; Henry Berger, Durham, both of N.C.

[73] Assignee: The BOC Group, Inc., New Providence, N.J.

[21] Appl. No.: 787,492

[22] Filed: Nov. 4, 1991

[51] Int. Cl.⁵ .............................................. G01N 25/26
[52] U.S. Cl. .................................................. 73/29.01
[58] Field of Search ...................................... 73/29.01

[56] References Cited

U.S. PATENT DOCUMENTS

| | | | |
|---|---|---|---|
| 3,665,748 | 5/1972 | Mator | 73/29.01 |
| 4,131,011 | 12/1978 | Ling | 73/29.01 |

Primary Examiner—Hezron E. Williams
Assistant Examiner—Joseph W. Roskos
Attorney, Agent, or Firm—David M. Rosenblum; Larry R. Cassett

[57] ABSTRACT

The present invention provides a method of performing an instantaneous moisture concentration measurement of a gas having a rapidly changing moisture concentration. This method has direct application to a method of determining the drydown characteristics of an environment in which a series of instantaneous moisture concentration measurements are made during the drying of the environment. In accordance with the present invention, a standard gas is generated having a known moisture concentration estimated to be essentially equal to the instantaneous moisture concentration of the gaseous fluid (which could be a purge gas used in drying an environment) at a selected instant of its rapidly changing moisture concentration. The standard gas is then sampled. At the selected instant, the gaseous fluid is sampled and its instantaneous moisture concentration is compared with the known moisture content of the standard gas. If essentially no difference exists, the known moisture will be essentially equal to the instantaneous moisture concentration. If a difference exits, the standard gas can be successively reformed with the known moisture concentration adjusted to eliminate the difference and thus provide an indirect measurement of the moisture concentration within the gas.

7 Claims, 3 Drawing Sheets

METHOD OF PERFORMING AN INSTANTANEOUS MOISTURE CONCENTRATION MEASUREMENT AND FOR DETERMINING THE DRYDOWN CHARACTERISTICS OF AN ENVIRONMENT

BACKGROUND OF THE INVENTION

The present invention provides a method of performing an instantaneous moisture concentration measurement of a gas having a rapidly changing moisture concentration. Additionally, the present invention relates to a method of determining the drydown characteristics of an environment by performing a plurality of instantaneous moisture concentration measurements of a purge gas used in drying the environment. More particularly, the present invention relates to such methods in which the instantaneous moisture concentration of the gas is determined through comparison with a standard gas having a known moisture concentration.

It is required that in some processes, semiconductors be manufactured in environments containing essentially no moisture. The moisture level in such manufacturing environments is however, not always stable. For instance, process chambers of rapid thermal processers are exposed to room ambient during the process loading cycle. After the loading cycle, the moisture concentration inside of the process chamber is reduced by introduction of purge gas into the process chamber. The changing moisture concentration of such an environment, termed in the art as the "drydown" characteristic of the chamber, is visualized by plotting a curve of purge exhaust gas moisture concentration versus time.

A typical method of defining such a curve is to connect a probe of a moisture analyzer to an exhaust outlet of the process chamber and to simply plot a curve of the probe output verses time after door closure. Using this method, the probe is also exposed to the rapidly decreasing moisture concentration of the purge gas and thus, its drydown characteristics will effect the accuracy of the curve. Put quite simply, the moisture concentration of the purge gas emanating from the chamber exhaust outlet can change far more rapidly than the probe is able to respond to such change.

As will be discussed, the present invention does not involve direct measurement of the moisture concentration of a gas. Rather, it allows for instantaneous concentration measurements to be made that are not dependent upon the response characteristics of the moisture analyzer used in making the measurements. A series of such measurements can then be used to generate a drydown curve of for instance, the process chamber of a rapid thermal processer.

SUMMARY OF THE INVENTION

The present invention provides a method of performing an instantaneous moisture concentration measurement of a gaseous fluid having a rapidly changing moisture concentration. In accordance with such method, a moisture concentration of the gaseous fluid is estimated at a selected instant of its rapidly changing moisture concentration and a standard gas is formed having a known moisture content equal to the estimate. The standard gas is sampled and then, the gaseous fluid is sampled so that it has a level of moisture concentration substantially equal to the moisture concentration thereof at the selected instant. The level of moisture concentration of the gaseous fluid is then compared with a known moisture concentration of the standard gas to determine whether any difference exists therebetween. If any difference exists, the the moisture concentration concentration of the gaseous fluid at the selected instant is reestimated. The standard gas is then reformed so that it has a known moisture concentration substantially equal to the reestimate of the moisture concentration of the gaseous fluid. Thereafter, the sampling and comparison steps (described above) are repeated. The foregoing can be repeated as necessary to eliminate the difference. When no difference exists, the measure of the moisture concentration of the gaseous fluid will be essentially equal to the known moisture content of the standard gas.

In another aspect, the present invention relates to a method of determining the drydown characteristics of an environment dried with a purge gas. In accordance with such method, the instantaneous moisture concentration of the purge gas is determined at a plurality of time intervals during the drying of the environment. At any one of the time intervals, a moisture concentration of the purge gas is estimated and a standard gas is formed having a known moisture content equal to the estimate. The standard gas is sampled and the purge gas is passed through the environment. At the one time interval, the purge gas is sampled after having passed through the environment and its level of moisture concentration is compared with the known moisture concentration of the standard gas to determine whether any difference exists therebetween. If any difference exists, the the moisture concentration of the purge gas at the one time interval is reestimated. The standard gas is then reformed so that it has a known moisture concentration substantially equal to the reestimate of the moisture concentration of the purge gas. Thereafter, the sampling and comparison steps (described above) are repeated. The foregoing can be repeated as necessary to eliminate the difference. When no difference exists, the instantaneous moisture concentration of the purge gas, at the one time interval, will be essentially equal to the known moisture content of the standard gas.

In practice, the comparison between the unknown moisture level of the gaseous fluid (or purge gas) and the known moisture concentration of the standard gas is made by exposing a moisture analyzer to the standard gas and then the gaseous fluid and monitoring its electrical signal output which is referable to moisture concentration. After exposure of the moisture analyzer to the gaseous fluid or purge gas, the electrical signal output of the moisture analyzer will either change very slightly, away from the trend of the change in moisture concentration, or change more dramatically. The aforementioned slight change indicates that the known moisture content of the standard gas is essentially equal to the unknown moisture concentration of the gaseous fluid or purge gas. The more dramatic change will indicate a difference between the unknown moisture concentration of the gaseous fluid or purge gas and the known moisture concentration of the standard gas. As set forth above, if a difference is found to exist, the standard gas is reformed with the known moisture content thereof adjusted to eliminate the difference. Thereafter, the moisture analyzer is reexposed to the standard gas and the gaseous fluid until the slight change in signal is produced. As such point, the known moisture content of the standard gas will be essentially equal to the unknown, moisture concentration of the gaseous fluid at the selected instant. Hence, the present invention allows for an indirect measurement of moisture concentration to be made that is independent of and not hampered by the response characteristics of a particular moisture analyzer.

BRIEF DESCRIPTION OF THE DRAWINGS

While the specification concludes with claims distinctly pointing out the subject matter than Applicants regard as their invention, it is believed that the invention will be better understood when taken in conjunction with the accompanying drawings in which:

DETAILED DESCRIPTION

Figure 1:
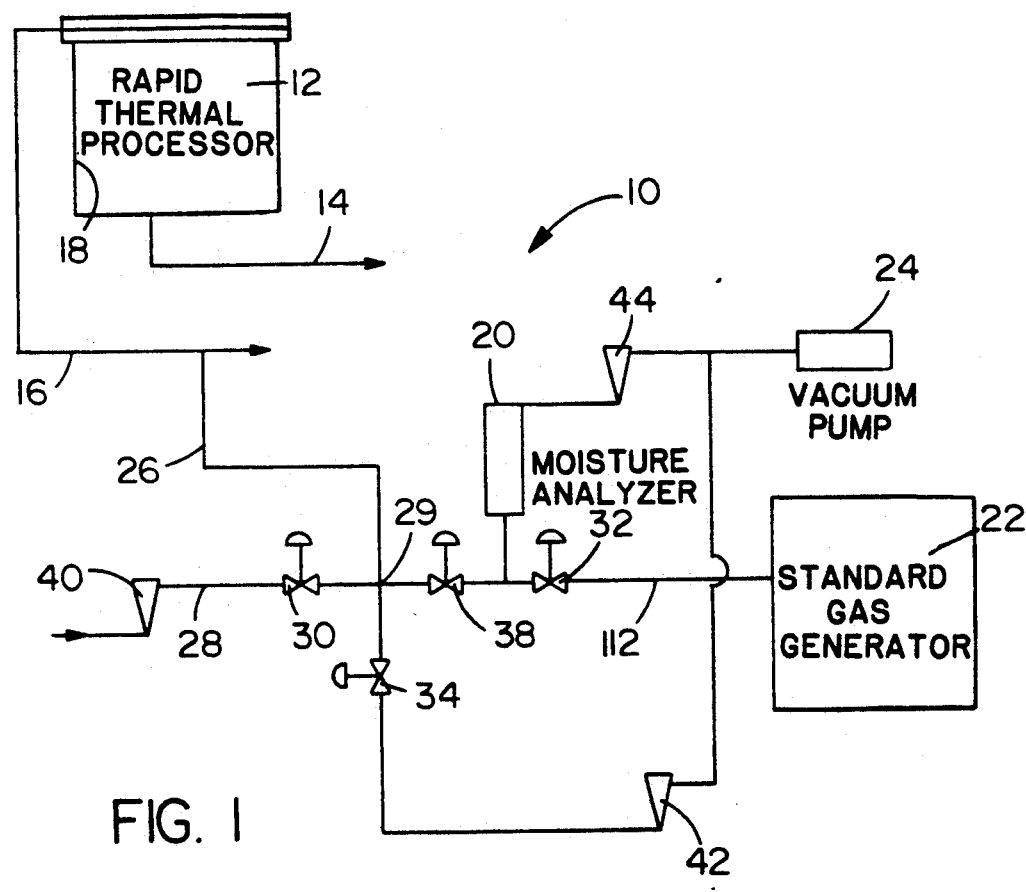
FIG. 1 is a schematic view of an apparatus for performing an instantaneous moisture concentration measurement of a gas.

With reference to FIG. 1, an apparatus 10 for performing an instantaneous moisture concentration measurement of a gas is illustrated. The gas emanates from a rapid thermal processor 12. Rapid thermal processor 12 has a chamber inlet line 14 and a chamber vent line 16 from which a nitrogen purge gas laden with room air moisture is discharged from a chamber 18 of rapid thermal processor 12.

As can be appreciated, after a door (not illustrated) of rapid thermal processor 12 opens and closes, nitrogen gas flowing through chamber vent line 16 at first has a relatively high concentration of moisture which rapidly tapers off. Apparatus 10 will be described as measuring the instantaneous moisture concentration of the nitrogen gas flowing through chamber vent line 16 of rapid thermal processor 12 for exemplary purposes only. Apparatus 10, as could be well appreciated, could be used to sample and measure the instantaneous moisture concentration of a gas from other sources.

Apparatus 10 includes a moisture analyzer 20 which can be a System II Moisture Probe manufactured by Panametrics Inc. of 221 Crescent Street, Waltham, Mass. 02554. A flow passage network is provided for ultimately conducting a standard gas generated by a standard gas generator 22 and nitrogen purge gas flowing through chamber vent line 16 to moisture analyzer 20. Such nitrogen purge gas and standard gas is drawn through moisture analyzer 20 by a vacuum pump 24. Nitrogen gas flowing through chamber vent line 16 enters apparatus 10 via sampling line 26. Additionally, a dry nitrogen purge gas (that is one having a lower moisture concentration than the maximum expected in the nitrogen purge gas used in drying chamber 18 of rapid thermal processor 12) can be introduced into sampling line 26 via a purge line 28 at a junction 29. The flows within the flow passage network are controlled by a cut off valve 30 to control the flow of the dry nitrogen purge gas, a cut off valve 32 to control the flow of the standard gas to moisture analyzer 20, a cut off valve 34 to control the flow of the nitrogen purge gas to be measured, and a cut off valve 38 to control the flow of the nitrogen purge gas to moisture analyzer 20.

Apparatus 10 also includes a set of three variable area flow controllers 40, 42 and 44. Flow controller 40 it attached to purge line 28, flow controller 42 is attached in sample line 26, and flow controller 44 connects moisture analyzer 20 to vacuum pump 24. Variable area flow controllers 40, 42, and 44 permit the flow rates within purge line 28, sample line 26 and moisture analyzer 20 to be preset.

Standard gas generator 22 will be discussed in greater detail hereinafter. At this point it is to be noted that it is capable of delivering standard gas, in this case nitrogen, having a preset known moisture concentration. In a standby state of apparatus 10, the preselected standard gas is formed with a preselected known moisture content that is set at a level estimated to be the moisture concentration of the nitrogen purge gas flowing from rapid thermal processor 12 at a selected instant in time.

While the standard gas is being formed, cut off valve 30 is open to allow dry nitrogen purge gas to enter sample line 26. After the standard gas is formed, cut off valve 32 is opened so that the standard gas is drawn from standard gas generator 22 through moisture analyzer 20. At this point of operation, cut off valves 34 and 38 are closed.

The door of rapid thermal processor 12 is then opened to load in a wafer. After the door is closed, valves 30 and 38 are closed, while valve 34 is opened to draw a sample of nitrogen gas flowing through chamber vent line 16 of rapid thermal processor 12 to vacuum pump 24. At a selected instant of time during the drydown cycle of rapid thermal processor 12, valve 34 is then closed along with valve 32, and valve 38 is opened to sample the instantaneous moisture concentration of the nitrogen gas flowing from rapid thermal processor 12.

Moisture analyzer 20 develops an electrical output signal that is referable to the moisture concentration in the gas that it is sampling. In this regard, moisture analyzer 20 can be programmed to read dew point temperature or concentration. Preferably moisture analyzer 20 is set to provide a dew point reading. If upon opening valve 38, the signal begins to rise, it is known that the nitrogen purge gas has a higher concentration than the known moisture concentration of the standard gas. If the signal output of moisture analyzer 20 falls, it is known that the moisture concentration of the nitrogen purge gas is lower than the known moisture concentration of the standard gas. If the signal level slightly increases, that is a 1° C. increase is indicated, it is known that the moisture concentration of the nitrogen purge gas is essentially equal to the known concentration of the sample gas. Since the moisture concentration of the nitrogen purge gas drying chamber 18 of rapid thermal processor 12 is decreasing over time, a slight decrease in signal level would not be indicative of equality between the unknown moisture concentration of the nitrogen purge gas and the known moisture concentration of the standard gas. In fact at such a reading of moisture analyzer 20, the moisture content of the nitrogen purge gas might in fact be far less than the moisture content of the standard gas. Here it is appropriate to point out that in other applications of apparatus 10 involving measuring the moisture concentration of a gas having a rapidly increasing moisture content, a slight decrease in signal level would be seen as indicative of equality between the unknown moisture concentration of particular gas to be measured and the known moisture content of the standard gas. In any case, when the known concentration of the sampling gas is essentially equal to the unknown instantaneous moisture concentration of the gas to be measured, the unknown instantaneous moisture concentration is thus measured.

If a difference exists, the process outlined above is repeated, except that sample gas generator 22 is then reset to form the sample gas with a moisture content that is adjusted toward the unknown instantaneous moisture content. For instance, it is was determined that a known concentration was previously below the unknown instantaneous concentration of the nitrogen purge gas, the known gas concentration would be increased. The reverse process would take place in case a known concentration were found to be above the instantaneous concentration of the nitrogen purge gas.

After the readjustment in the known concentration, valves 30, 32, 34 and 38 are then reset to the standby state, the door is again opened to load a wafer. After closure of the door, cut off valve 30 is then closed while cut off valve 34 is opened to draw a sample through sample line 26 to vacuum pump 24. Again, at the selected instant of the dry down cycle of thermal processor 12, valve 34 is then closed, while valve 38 is opened to sample the moisture concentration of the nitrogen purge gas being expelled from rapid thermal processor 12. Several of the same iterations are then made to determine a single selected instant in the dry down of rapid thermal processor 12. As may be appreciated, the moisture concentration of nitrogen gas emanating from rapid thermal processor 12 is then tested at other selected instances to determine several data points that are plotted as a curve of the drydown characteristics of rapid thermal processor 12.

Rapid thermal processor 12 has a unique drydown characteristic following door closure and as such, its door can be repeatedly closed and the moisture concentration of the nitrogen purge gas can be repeatedly tested at any specific instant or time interval following door closure. Thus, apparatus 10 is designed to directly sample the nitrogen purge gas from rapid thermal processor 10 each time a test is to be made. Although not illustrated, but as could be appreciated by those skilled in the art, provision could be made in apparatus 10 to store a sample of the nitrogen purge gas emanating from rapid thermal processor 12 (or for that matter other gaseous fluids issuing from other process equipment) in a plenum or other gas storage device. In such case, the particular gas to be tested would be repeatedly sampled from the gas storage device rather than directly from the process equipment of interest.

Figure 2:
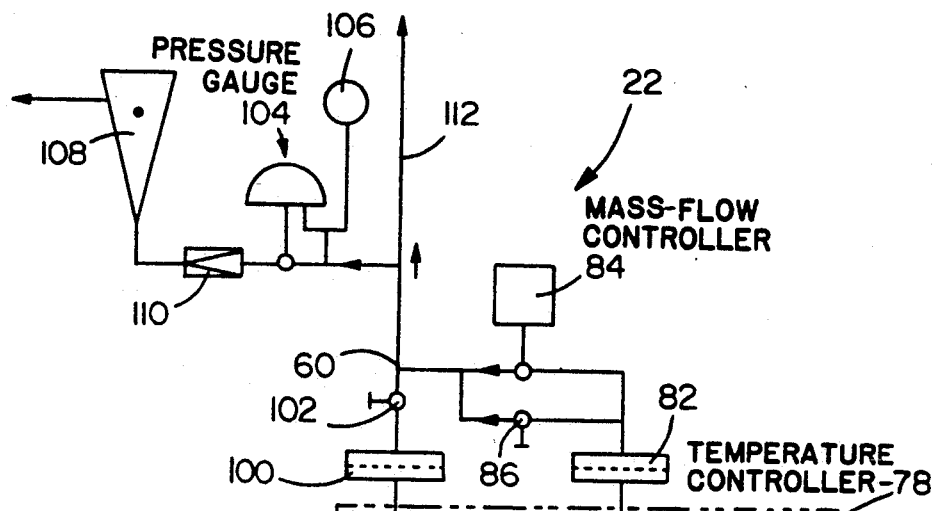
FIG. 2 is a schematic illustration of an apparatus used for generating a standard gas used in the apparatus illustrated in FIG. 1.
Figure 2:
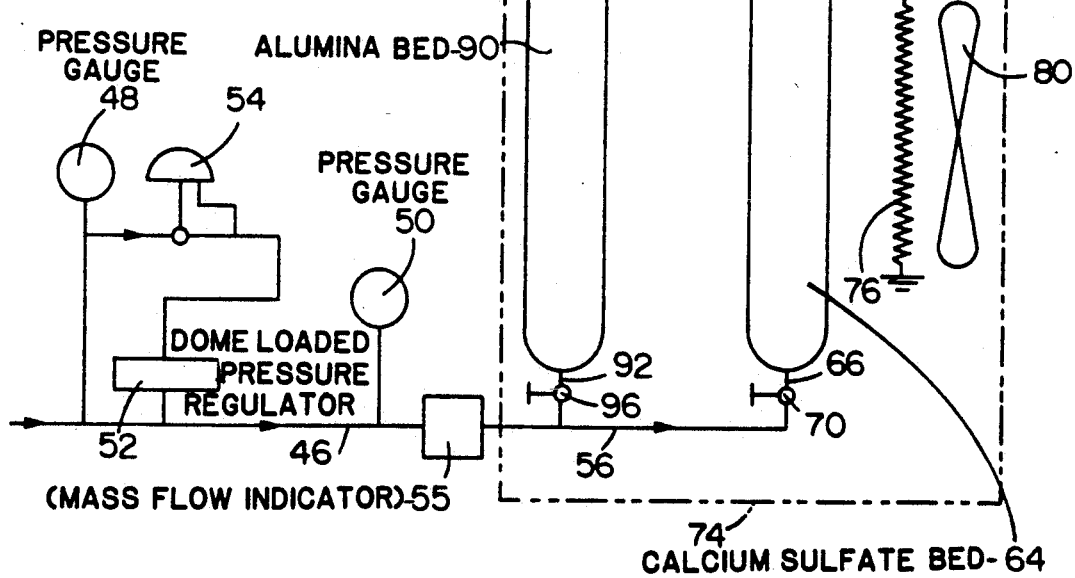

The detailed construction of standard gas generator 22 is illustrated in FIG. 2. It is designed to produce a mixture of nitrogen gas and moisture at variable, known low level concentrations. Standard gas generator 22 is the subject of U.S. patent application, entitled "Mixture Forming Method And Apparatus", filed Oct. 30, 1991, Ser. No. 07/784,826 and owned by the BOC Group, Inc. of 575 Mountain Ave., Murry Hill, N.J. 07974, the assignee herein. It should be mentioned that other prior art blending equipment could be used in forming the requisite standard gas.

Nitrogen enters standard gas generator 22 through an entry leg 46 containing a source pressure gauge 48 for registering the pressure of the nitrogen at its source. Pressure within entry leg 46 is registered by an inline pressure gauge 50. Both source and inline pressure gauges 48 and 50 are capable of registering pressure in an approximate range of between 0 and 100 psi. Pressure is controlled within entry leg 46 by a dome loaded pressure regulator 52. Such a pressure regulator is used because it can be manufactured to be completely compatible with high purity applications. However, it does require a reference pressure. Such reference pressure is provided by an instrument grade pressure regulator 54. This pressure regulator is capable of holding a constant pressure but it is not compatible with high purity gas systems and as such is connected to dome loaded pressure regulator 52 to simply set its reference pressure. The total flow rate of nitrogen within entry leg 46 is registered by a thermal type mass flow indicator 55.

Entry leg 46 comprises one of three legs of a branched flow path. The branched flow path contains primary and secondary legs, which will be described in more detail hereinafter, branching off from entry leg 46 at a first junction 56 and rejoining one another at a second junction 60. In the most common practice of the present invention, as has been discussed above, the major portion of the nitrogen will flow in the primary leg.

The secondary leg is formed by a bed 62. Bed 62 comprises a cylinder 64 having an inlet 66 and an outlet 68. Bed 62 can isolated by a pair of inlet and outlet cutoff valves 70 and 72. Bed 62 contains approximately 0.5 liters of calcium sulfate, preferably non-indicating DRYERITE, mesh #10-20, manufactured by W. A. Hammond Dryerite Company, P.O. Box 460, Xenia, Ohio 45385. Although not illustrated, the calcium sulfate is held within cylinder 64 between two screens near inlet 66 and outlet 68, respectively. Bed 62 is prepared by first fully hydrating the calcium sulfate. This is accomplished by spreading the calcium sulfate on a tray into a layer of about 6.35 mm. thick and exposing it to the ambient for about 24 hours. During such exposure, the calcium sulfate is covered with filter paper. Thereafter, cylinder 64 is filed and inlet and outlet cutoff valves 70 and 72 are installed. A flow of dry gas is then passed through cylinder 64, through inlet 66 and out of outlet 68, at a flow rate of about 4 to 5 liters per minute for about a week or two. The moisture content of the flow passing from bed 62 is monitored and when stable, is compared with a flow from a previously prepared cylinder that has been similarly run for about a year. When no difference in moisture content is observed, it is known that absorbed impurities have been removed from the bed and also, that the bed is partially hydrated and contains two solid phases. It is important to note that the bed must then be used so that the flow passes through the bed in the same direction as the flow used in preparing the bed. One of the solid phases contains water in accordance with the formula $CaSO_4 \cdot \frac{1}{2} H_2O$. The water existing within this solid phase is in equilibrium with water in a vapor phase. The other of the solid phases may be completely dehydrated or in fact may contain water and calcium sulfate in some other molar proportion.

Bed 62 is then calibrated. Normally such calibration is carried out with the bed held at a controlled temperature of approximately 25° C. Ultra high purity dry nitrogen gas is then passed through the bed and then through a $\frac{1}{8}$ inch outer diameter copper tube approximately 20 inches long contained within a constant temperature bath machine, which is well known in the art. From the copper tube, the gas flows through a stainless steel filter and a moisture analyzer (preferably identical to moisture analyzer 20). Thereafter, the flow is conducted through a flow meter. The bath machine is then cooled while moisture is measured by the probe. At some point, there will a appear a fall off in moisture content as indicated by a decreasing probe signal. This "fall off" point is the dew point temperature at which an equilibrium exists between the solid and vapor phases of the water contained within the nitrogen flow. The partial pressure of the water within the flow, and therefore within the bed, is a well known function of this dew point temperature and as such, will become a known quantity at a bed temperature of approximately 25° C.

This vapor phase pressure will remain constant so long as bed 62 is used at about 25° C. In this regard, the bed temperature of bed 62 is maintained constant within a temperature controlled cavity indicated by dashed line 74, and a heater 76 coupled to a temperature controller 78. Ambient air is blown through temperature controlled cavity 74 by a motorized fan 80.

The flow of the nitrogen moisture mixture then passes into a model 55-4FW-.5 all metal filter 82 manufactured by Nupro Co. of 4800 East 345th Street, Willoughby, Ohio 44094 which is used to filter any small particles of bed 62 passing from cylinder 64. Thereafter, the mixture can flow into two sub-branches formed by a mass flow controller 84 and a needle valve 86 located near second junction 60.

The mixture flowing from bed 62 is diluted by nitrogen flowing through a primary leg of the aforementioned branched flow path formed by a bed 88 containing approximately 0.5 liters of activated alumina A-2, 12-32 mesh (manufactured by La Roach Chemical Company, P.O. Box 1031, Baton Rough, La. 70812) within a cylinder 90. Cylinder 90 is approximately 35.0 cm long and 5.0 cm in diameter and is provided with an inlet 92 and an outlet 94.0 Cylinder 90 can be isolated by inlet and outlet cut off valves 96 and 98. An all metal filter 100, identical in construction to filter 82, can be used to filter out any small particles of alumina passing from cylinder 90. The flow within such primary leg is controlled by a needle valve 102. Since the flow in the primary leg can either be adjusted by flow controller 84 or needle valve 86, adjustment of needle valve 102 will in turn control not only the flow rate in the primary leg of the branched flow path but also the total flow rate through apparatus 10.

A back pressure controller 104 is provided which is set with reference to a pressure gauge 106 having an approximate scale range of 0 to 50 psi. Any excess pressure of the nitrogen and moisture mixture would be vented through variable area flow meter 108 to sense flow rate. A check valve 110 is provided to prevent atmospheric ambient from entering standard gas generator 22 when not in use.

The standard gas is delivered from outlet line 112. The moisture concentration of the standard gas will be equal to the bed partial pressure divided by the total gas pressure as sensed by pressure gauge 50 multiplied by the flow rate set by mass flow controller 84 divided by the total flow rate set by needle valve 102. It is noted here that in the moisture concentrations to be developed by standard gas generator 22, needle valve 86 will be closed.

Figure 3:
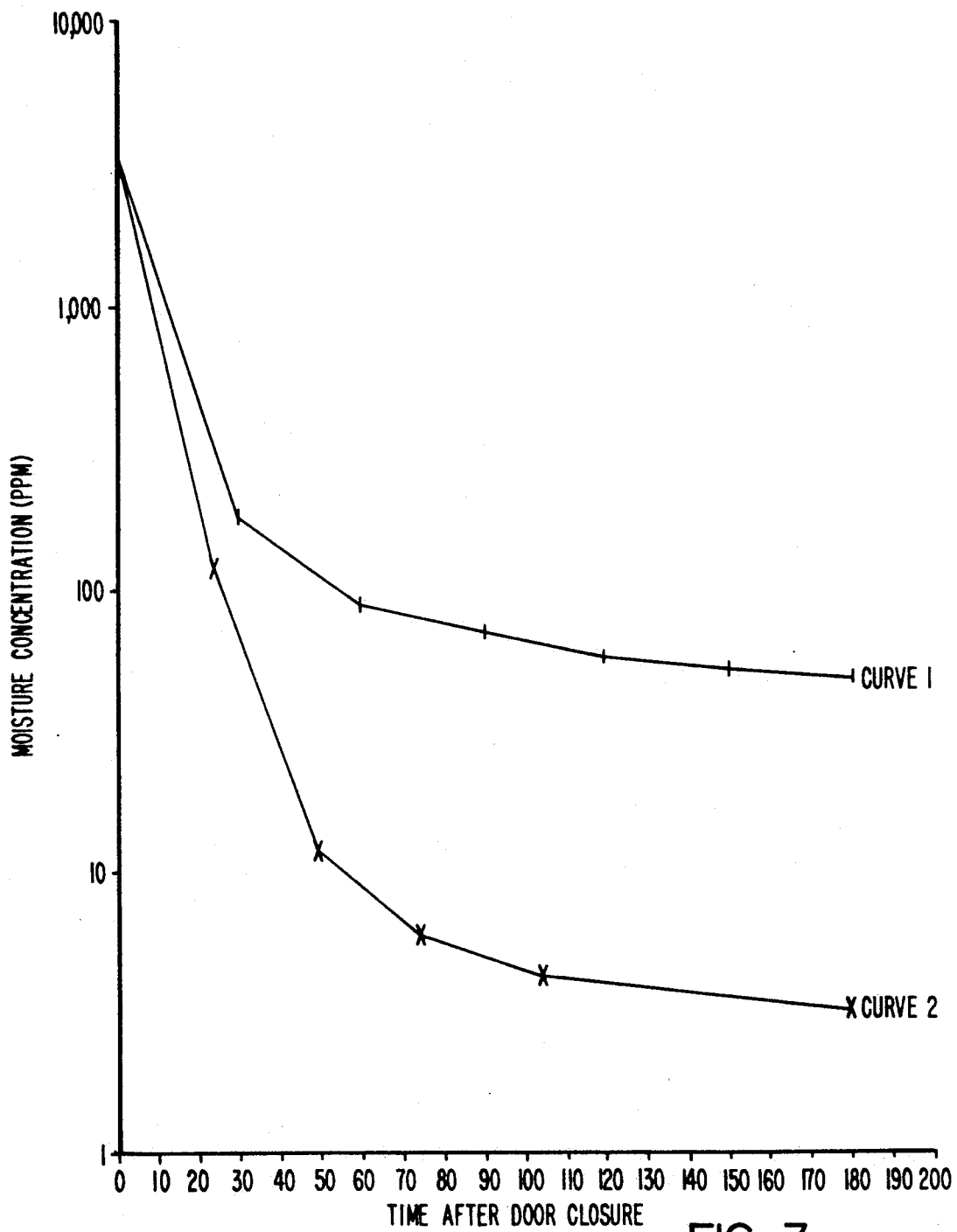
FIG. 3 is a graph of the drydown characteristics of a rapid thermal processer comparing apparatus and methodology of the present invention with the prior art.

With reference to FIG. 3, drydown curves for rapid thermal processing chamber 12 were produced, first by prior art methodology (Curve 1) and then by the method of the present invention, (Curve 2). Curve 1 was derived by simply exposing a Panametrics Probe, such as described above, to purge gas emanating from chamber vent line 16 of rapid thermal processor 12 and noting the moisture concentration as read from the probe. Curve 2, which is more accurate than Curve 1, was produced by taking several moisture concentration measurements in accordance with the method of the present invention 1.

In order to further understand the method of the present invention and in particular the use of standard gas generator 22, the moisture concentration measurements used in forming Curve 2 will be discussed. As is indicated on Curve 2, measurements were taken at 25, 50, 75, 105, and 180 seconds following door closure. During all measurements, flow controllers 40 and 44 were set at 1 liter/min., while flow controller 42 was set at 200 cc/min to prevent stagnation within sample line 26.

Using the 75 second measurement as an example, as a first step, the moisture concentration was estimated to be −67° C. on the basis of the previous measurement at 50 seconds which was measured as containing moisture at a dew point of 59° C. or 12 ppm. Standard gas generator 22 was then set up to deliver the standard gas containing moisture at a dew point of −67° C. In this regard, needle valve 86 was closed and needle valve 102 and mass flow controller 84 were adjusted by trial and error to produce the standard gas at the requisite moisture level. During the set up of standard gas generator 22, valve 30 was opened to purge line 26, valves 34 and 38 were closed, and valve 32 was open to continually monitor the moisture content within the standard gas.

The door of rapid thermal processor 12 was then opened and closed. Immediately after door closure, valve 30 was closed and valve 34 was opened to draw a sample of the nitrogen purge gas to junction 29. Approximately 30 seconds later, valves 34 and 32 were closed and valve 38 was opened to sample the nitrogen purge gas. A chart recorder, connected to the output of moisture analyzer 22, indicated an increase from −67° C. to −65° C. Apparatus 10 was then switched back to a standby mode with valves 30 and 32 open and valves 34 and 38 closed. Thereafter, standard gas generator 22 was again readjusted to produce a standard gas containing moisture at a dew point of about −64.5° C. The process outlined above was repeated with this reformed standard gas. The result was a stable peak at −64° C., and a peak width of about 90 seconds. The moisture concentration, deduced from that of the standard gas, was therefore found to be 6.0 ppm at about 75 seconds following door closure (that is 30 seconds plus one-half 90 seconds).

In the above example, the first estimate of the moisture concentration of the nitrogen purge gas was based upon the previous measurement. The first measurement, at 25 seconds, was estimated on the basis of the response characteristics of moisture analyzer 22. In this regard, the door of rapid thermal processor was opened and closed. About 5 seconds after door closure, the nitrogen purge gas was sampled by opening valve 38 with valves 30, 32, and 34 closed. The result response curve of moisture analyzer 22 showed a peak width of approximately 40 seconds. The first estimate of moisture concentration following door closure was selected to be the height of the peak.

It should be mentioned that all initial estimates of the unknown moisture concentration of the nitrogen purge gas could have been made as outlined directly above. This was not done because of the time involved in forming initial estimates in such a manner. Additionally, Curve 2 could have been derived by estimating the moisture content at a set of arbitrary time intervals and thereafter manipulating standard gas generator until a 1° C. increase (or less) was seen in the signal generated by moisture analyzer 20 upon switchover from the standard gas to the nitrogen purge gas. As may be appreciated, the derivation of Curve 2 in such a manner would take far longer than the more efficient method outlined above.

While the invention has been shown and described with reference to a preferred embodiment, as will occur to those skilled in the art, numerous additions and changes may be made without departing from the spirit and scope of the present invention.

We claim:

1. A method of performing an instantaneous moisture concentration measurement of a gaseous fluid having a rapidly changing moisture concentration, said method comprising the steps of:
    (a) estimating a moisture concentration of the gaseous fluid at a selected instant of its rapidly changing moisture concentration;
    (b) forming a standard gas having a known moisture content equal the estimate;
    (c) sampling the standard gas;
    (d) sampling the gaseous fluid so that it has a level of moisture concentration substantially equal to the moisture concentration thereof at the selected instant and comparing its said level of moisture concentration with the known moisture concentration of the standard gas to determine whether any difference exists therebetween; and
    (e) if any said difference exists, eliminating the said difference by repeatedly performing the following steps as necessary: reestimating the moisture moisture concentration of the gaseous fluid at a selected instant, reforming the standard gas so that the known moisture concentration is substantially equal to the reestimate in the moisture concentration of the gaseous fluid, and repeating steps c) and d), whereby when essentially no said difference exists, the measure of the moisture concentration of the gaseous fluid will be essentially equal to the known moisture content of the standard gas.

2. The method of claim 1, wherein:
the level of the moisture concentration of the gaseous fluid and the known moisture content of the standard gas is compared in a moisture analyzer having means for generating an electrical signal which increases if the level of the moisture concentration of the gaseous fluid is greater than the known moisture content of the standard gas and which decreases if the level of the moisture concentration of the gaseous fluid is less than the moisture content of the standard gas;
the signal is monitored to determine whether the said difference exists;
the known moisture content of the standard gas is decreased in case of an increasing signal and is increased in case of a decreasing signal during reformation of the standard gas.

3. The method of claim 1, wherein:
the gaseous fluid can be repeatedly reformed with the rapidly changing moisture concentration; and
if the said difference exists, the gaseous fluid is repeatedly reformed and resampled at the selected instant.

4. The method of claim 3, wherein:
the level of the moisture concentration of the gaseous fluid and the known moisture content of the standard gas is compared in a moisture analyzer having means for generating an electrical signal which increases if the level of the moisture concentration of the gaseous fluid is greater than the known moisture content of the standard gas and which decreases if the level of the moisture concentration of the gaseous fluid is less than the moisture content of the standard gas;
the signal is monitored to determine whether the said difference exists;
the known moisture content of the standard gas is decreased in case of an increasing signal and is increased in case of a decreasing signal during reformation of the standard gas.

5. A method of determining the drydown characteristics of an environment dried with a purge gas, said method comprising:
determining instantaneous moisture concentrations of the purge gas at a plurality of time intervals during the drying of the environment; and
at any one of the time intervals:
    (a) estimating an initial moisture concentration of the purge fluid at the one time interval;
    (b) forming a standard gas having a known moisture content equal the estimate;
    (c) sampling the standard gas;
    (d) passing the purge gas through the environment;
    (e) at the one time interval, sampling the purge gas after having passed through the environment and comparing its said level of moisture concentration with the known moisture concentration of the standard gas to determine whether any difference exists therebetween;
    (f) if any said difference exists, eliminating the said difference by repeatedly performing the following steps as necessary: reestimating the moisture moisture concentration of the purge gas at the one time interval, reforming the standard gas so that the known moisture concentration is substantially equal to the reestimate in the moisture concentration of the gaseous fluid, and repeating steps c), d) and e), whereby when no said difference exists, the instantaneous moisture concentration of the purge gas, at the one time interval, will be essentially equal to the known moisture content of the standard gas.

6. The method of claim 5, wherein:
the level of the moisture concentration of the purge gas and the known moisture content of the standard gas is compared in a moisture analyzer having means for generating an electrical signal which increases if the level of the moisture concentration of the purge gas is greater than the known moisture content of the standard gas and which decreases if the level of the moisture concentration of the purge gas is less than the moisture content of the standard gas;
the signal is monitored to determine whether the said difference exists;
the known moisture content of the standard gas is decreased in case of an increasing signal and is increased in case of a decreasing signal during reformation of the standard gas.

7. The method of claim 6, further comprising:
preselecting the time intervals at which the instantaneous moisture concentrations are to be determined by:
exposing the moisture analyzer to a gas having a low moisture concentration, below an expected maximum moisture concentration of the purge gas, at a series of selected times, exposing the moisture analyzer to the purge gas, recording a width of a peak signal at each of the selected times, and deriving the preselected time intervals by adding to each of the selected times, one-half of the width of the peak signal; and estimating the initial moisture concentration of the purge gas at a first of the preselected time intervals to be equal to a peak of the peak signal associated with the first of the preselected time intervals.

* * * * *